United States Patent [19]

Rueter

[11] Patent Number: 4,523,593

[45] Date of Patent: Jun. 18, 1985

[54] CONSTANT A-A INTERVAL CONTROL FOR DVI AND DDD CARDIAC PACEMAKERS

[75] Inventor: John C. Rueter, Shoreview, Minn.

[73] Assignee: Medtronic, Inc., Minneapolis, Minn.

[21] Appl. No.: 504,709

[22] Filed: Jun. 15, 1983

[51] Int. Cl.³ .............................................. A61N 1/36
[52] U.S. Cl. ............................................ 128/419 PG
[58] Field of Search ................................. 128/419 PG

[56] References Cited

U.S. PATENT DOCUMENTS

| | | | |
|---|---|---|---|
| 4,378,020 | 3/1983 | Nappholz et al. | 128/419 PG |
| 4,412,541 | 11/1983 | Schalbach et al. | 128/419 PG |
| 4,421,116 | 12/1983 | Markowitz | 128/419 PG |

Primary Examiner—William E. Kamm
Attorney, Agent, or Firm—Glenn W. Bowen; John L. Rooney; Joseph F. Breimayer

[57] ABSTRACT

A physiologic cardiac pacer operable in the DVI or A-V sequential pacing mode or the DDD or fully automatic pacing mode senses for the omission of an R-wave from an implantable cardiac pacer during the A-V interval. If the pacer does not sense a R-wave during the A-V interval the V-A interval is timed out immediately following the A-V interval and an atrial pacing pulse is issued at the end of the V-A interval. In the event, however, that an R-wave is sensed during the V-A interval, a flag is set and then the entire A-V interval is to be timed out, at which time the state of the flag is determined. If an R-wave was previously issued, a ventricular pacing pulse is not issued to the pacer at the end of the A-V interval, whereas if the flag is not set it is transmitted to the pacer.

2 Claims, 5 Drawing Figures

CONSTANT A-A INTERVAL CONTROL FOR DVI AND DDD CARDIAC PACEMAKERS

BACKGROUND OF THE INVENTION

The present invention relates to cardiac pacemakers of the physiological type, particularly those which operate in the DDD and DVI modes.

Pacing modalities of cardiac pacemakers are designated by a three-letter code which was authorized by the Inter-Society Commission for Heart Disease Resources as a standardized means of identifying the operation and mode of an implantable pulse generator. The first letter of this Code indicates the chamber which is paced. A capital V indicates the ventricle chamber, a capital A the atrium, and a capital D indicates that both chambers may be placed. The second letter employs the same designations and indicates whether the ventricle or the atrium alone is sensed, or whether both are sensed. The third letter of the code indicates the mode of response. A capital I indicates an inhibited mode, a capital T a triggered mode, and a capital D a "double mode." The double mode is more particularly defined as an atrial-triggered, ventricular-inhibited mode of operation.

In recent years the vast majority of electronic pacemakers which were implanted in cardiac patients were of the ventricular demand type. The three-letter pacing modality code for this type of pacemaker is VVI, which indicates that the ventricle is both paced and sensed, and that the pacing output of the implanted pacemaker is inhibited when a natural ventricular pulse is sensed by the artificial pacemaker. With the ventricular demand pacemaker, only a single lead is inserted in the ventricle and the pulses that occur naturally in the atrium are, therefore, not sensed. Modern physiological cardiac pacemakers are used with leads inserted into both the atrial and the ventricular chambers of the heart and rely on synchronization of timing cycles so that ventricular pulses occur at an appropriate time after the occurrence of atrial pulses. The proper timing between the atrial and the ventricular pulses is called A-V synchrony. By maintenance of proper A-V synchrony, an effective increase in cardiac output of up to 30 percent may be obtained. In other words, physiologic pacing can restore, to a large degree, the contribution of the atrium chamber, thereby achieving substantial hemodynamic improvement over VVI pacing and, in addition, a measure of control of cardiac arrhythmias can be obtained by these modern pacing modes.

There are three types of pacing modalities which are characterized as the physiological. The first is the atrail, or P-wave synchronous mode which is designated as the VDD mode. This means that both chambers are sensed, but only the ventricle chamber is paced.

The next physiological pacing mode is the A-V sequential pacing mode which is designated by the letters DVI. As indicated, this mode is one in which both chambers may be paced, but sensing occurs only in the ventricle chamber, and the occurrence of a natural pulse in the ventricle chamber during a predetermined timing cycle will inhibit pacing of the ventricle during that timing cycle.

The third physiological pacing modality is called the universal mode, or the DDD mode. This indicates that both chambers may be either sensed or paced, and the mode of response is atrial-triggered, ventricular-inhibited.

In prior physiologic cardiac pacemakers, the sensing of a natural atrial pulse, or P-wave, or the occurrence of a produced atrial pacing pulses serves to initiate the start of a timing period called the A-V interval. During the A-V interval, the ventricular sense amplifier is capable of sensing a naturally occurring ventricular pulse, or R-wave. In these prior cardiac pacemakers, if an R-wave is sensed during the A-V interval, a second time period called the V-A interval is immediately initiated, at the end of which an atrial pulse is generated. If the A-V interval times out without the sensing of an R-wave, however, the V-A interval begins at the end of the A-V interval.

The V-A interval was thus a fixed time interval in prior physiologic pacemakers, and the resulting A-A interval, which is total time period from the atrial pacing pulse that initiated the A-V interval and the end of the V-A interval, was variable when the V-A interval was initiated by an R-wave. The A-A interval, however, was fixed when it was started by a ventricular pacing pulse. (The interval between the start of the A-V interval and the occurrence of a R-wave is defined as the A-R interval). In cases where the patient's natural A-R interval became much less than the programmed A-V interval, the resulting pacing rate becomes much faster than intended, and this resulted in a serious potential hazard to the patient. The present invention resolves this serious problem found in prior physiologic cardiac pacemakers.

DESCRIPTION OF THE DRAWINGS

The present invention is described by reference to the drawings in which.

TECHNICAL DESCRIPTION OF THE INVENTION

Figure 1:
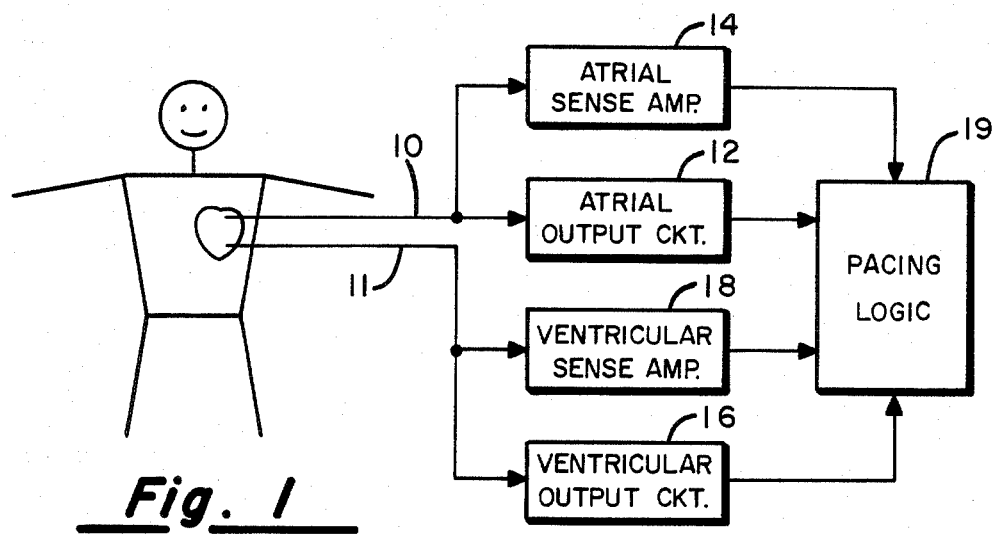
FIG. 1 is a block diagram which represents the implementation of the present invention.

The problem described in the Background of the Invention section of this document may be better understood by reference to FIG. 1 which shows a timing diagram representation of prior cardiac pacemakers. One of the most important considerations in physiologic pacing is the ability to be able to maintain A-V synchrony. This means that the ventricle chamber of the heart must not be artificially paced until after the appropriate A-V interval has passed, in order to allow the heart to beat naturally whenever possible. Thus, during the A-V interval a naturally occurring ventricular pulse, or R-wave may be sensed. At the end of the A-V interval, if an R-wave is not sensed, the ventricle chamber will be paced.

The A-A interval of prior physiologic pacemakers was established by the summation of the time-out of a V-A interval counter plus the portion of the total programmed A-V interval that had elapsed at the time that either a R-wave or a ventricular pacing pulse occurred . If a R-wave occurred toward the end of an A-V interval, the A-A interval would vary somewhat, but the A-A interval variation would generally be small enough in this case so that it would not cause a significant detrimental effect on the patient being paced. However, as previously mentioned, when the patient's A-R interval was very short, so that it was much less than the programmed A-V interval, the result would be a shortening of the A-A interval substantially below the desired value.

Figure 2:
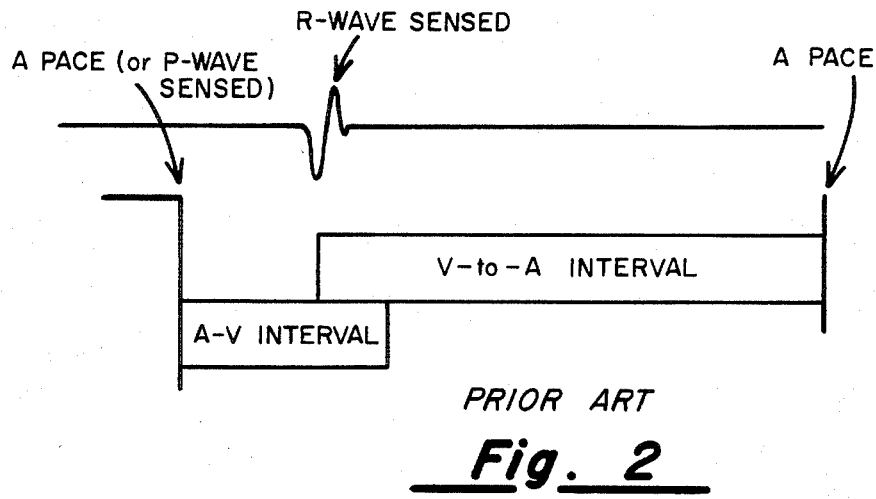
FIG. 2 is a timing diagram representative of prior physiologic cardiac pacemakers.

FIG. 2 shows a timing diagram associated with the present invention. The differences between the operation of the present invention and the previously described prior physiologic pacemakers is seen to be that, in the present invention, the A-A interval is always equal to the fixed A-V interval, plus the fixed V-A interval value. By contrast, with the implemented timing diagram of prior designs, it is seen that the A-A interval was fixed only when an R-wave was not sensed during the A-V interval, and this defect caused the previously mentioned potential patient hazard to arise, when there were long programmed A-V intervals and short A-R responses by the patient.

Figure 3:
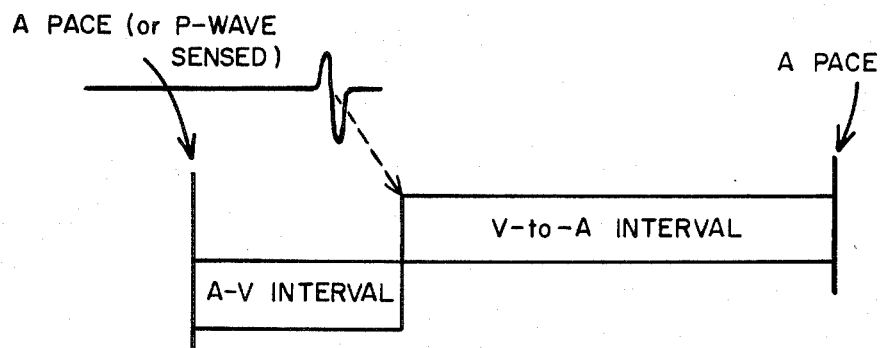
FIG. 3 is a timing diagram representative of a cardiac pacemaker constructed in accordance with the present invention.

FIG. 3 shows an implantable pacing generator 10 which is connected to the heart of a patient and which has an atrial output circuit 12 for supplying pulses to the heart, an atrial sense amplifier 14, a ventricular pulse output circuit and a ventricular sensing circuit 18. The pacemaker 10 employs pacing logic that implements the present invention, as represented by the flow chart of FIG. 4.

The present invention may be implemented through programming of a microprocessor of the type that is commonly employed in physiologic cardiac pacemakers, but it can also be implemented with circuitry if desired. The utilization of a microprocessor in an implanted pulse generator to implement the desired invention is best understood by reference to the flow chart of FIG. 4.

Figure 4:
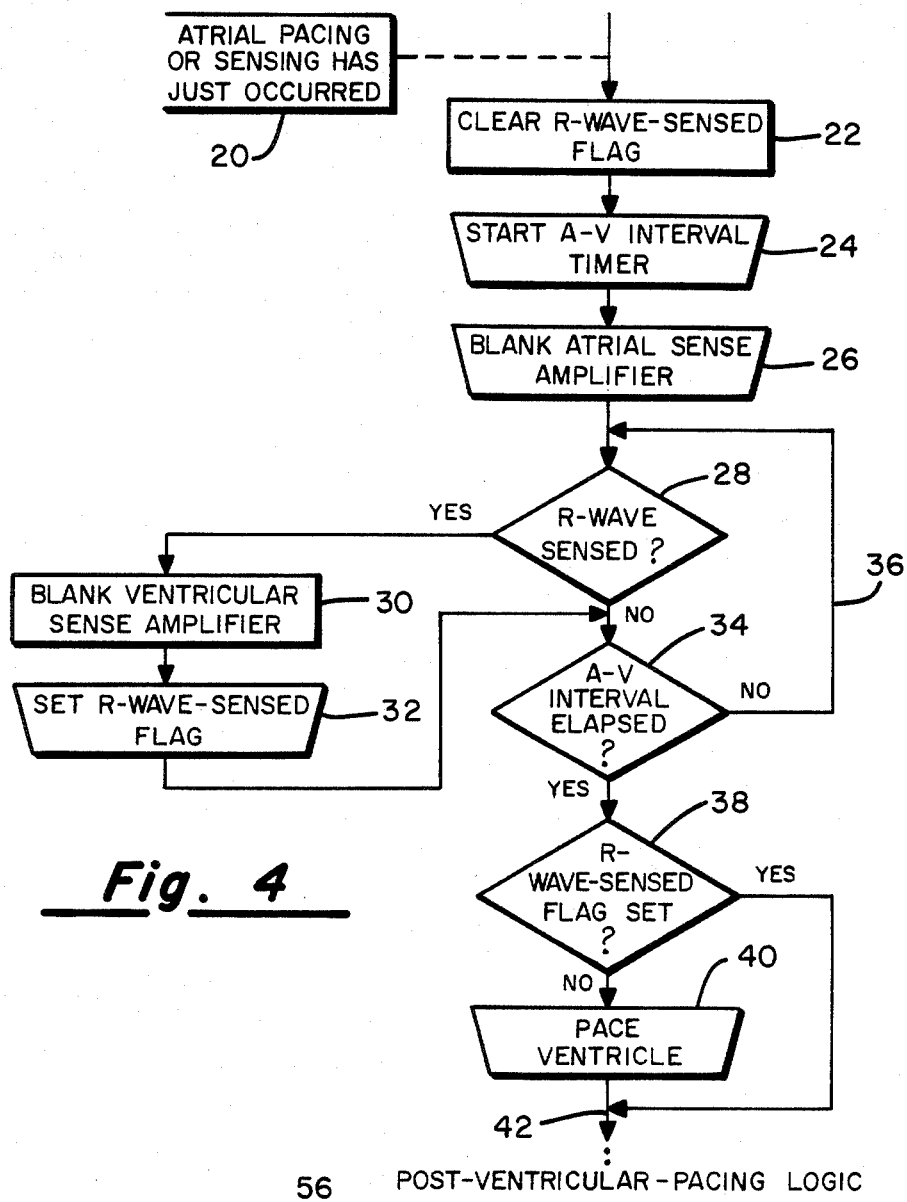
FIG. 4 is a flow chart representative of the implementation of the present invention.

The comment 20 indicates that an atrial pacing or sensing pulse has just occurred to initiate the desired subroutine of FIG. 4. In the present invention, whenever a natural or R-wave is sensed, a flat is set. The setting of a flag is equivalent to the setting of a flip-flop. Since this step merely uses a memory element to retain the knowledge that a particular event has occurred, the procedure of FIG. 4 requires clearing of the R-wave flag which was set up at a previous R-wave sensing occurrence, as indicated by operation step 22. The A-V interval timer is then started as indicated by the operation step 24. Starting of the A-V interval timer also causes the atrial sense amplifier to be blanked, so that whenever an R-wave occurs, there will be no false signals passing through the atrial sense amplifier as indicated by operation step 26.

The decision step 28 is dependent upon the ventricular sense amplifier sending its signal to the processor for detection in accordance with well-known procedures. Once the microprocessor determines that an R-wave has been sensed, the operation step 30 indicates that the ventricular sense amplifier will then be blanked since the next signal that is expected to be set will be an atrial pacing pulse, or alternately, a P-wave from the atrium. At the time the atrial sense amplifier is blanked, the R-wave sense flag is also set, as indicated by step 32. When the R-wave is no longer being sensed, the decision block 28 allows the procedure to step to the decision step 34 at which a test is made to see if the A-V interval has timed out.

The loop line 36 is connected back to the input of the decision block 28 until the A-V interval has completely elapsed. Upon the time-out of the A-V interval counter in the processor, the decision step 38 comes into operation. At this point, the microprocessor circuitry looks at the R-wave flag, or flip-flop, and determines whether it has been set. If the R-wave flag was set by the occurrence of a naturally-occurring R-wave, and the A-V interval timer has elapsed, the subroutine will exit, as indicated by exit line 42, to conventional post-ventricular pacing logic of the type employed in prior physiologic pacemakers and will bypass the operation step 40, since the occurrence of a natural R-wave does not require that the ventricle be paced artificially. In the event, however, that an R-wave was not sent by the time of decision step 38, the ventricle pulse generator will apply a pulse to the ventricle chamber.

It is seen, therefore, that the programming flow chart of FIG. 4 readily implements the desired timing of FIG. 3 by employment of a flag that, upon the sensing of the R-wave, causes the time-out of a V-A interval to be started only after the full A-V interval has been timed-out. This allows the A-A interval of the pacemaker of the present invention to be fixed at a constant time interval regardless of whether or not the pacemaker is sensing natural R-waves or supplying ventricular pulses.

Figure 5:
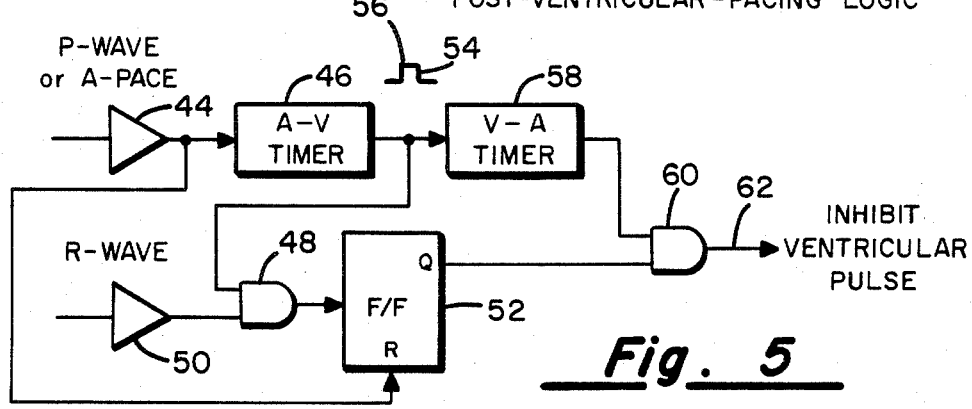
FIG. 5 is a block diagram of an alternate emobidment of the present invention.

An alternate embodiment of the present invention is described in reference to FIG. 5 wherein the circuit elements may be elements of the microprocessor employed in the pacemaker, or may be additional elements which have been added to the pacing circuitry if the processor does not have equivalent necessary elements incorporated therein. In the diagram of FIG. 5. An atrial sense amplifier 44 is coupled to an A-V timer 46. The A-V timer is coupled to an AND gate 48 and the other input of the AND gate 48 is coupled to the output of a ventricular sense amplifier 50. After the A-V timer is started, upon receipt of a P-wave by the amplifier 44, one input of the AND gate 48 will be actuated, and if an R-wave signal appears at the ventricle amplifier 50, a signal will be coupled through the AND gate 48 to set the R-wave flag, flip-flop 52. Thus, the flip-flop 52 may be set only upon the occurrence of a R-wave during the A-V interval.

Upon completion of the A-V time-out of the timer 46, the trailing edge 54 of the time-out pulse 56 from the A-V timer initiates the operation of the V-A timer 58. The Q output of flip-flop 52 activates one gate of the AND gate 60. If it has been set, and the other input of the gate 60 is coupled to the output of the V-A timer 58. The output of the AND gate 60 on the line 62 is the ventricular pulse inhibition signal, which is applied to the ventricular pulse generator to inhibit it whenever the V-A timer is timing out providing a flip-flop 52 was set indicating that a previous R-wave was received during the A-V interval. In the event the inhibit signal does not appear on the line 62, the ventricular pulse generator will be activated upon the completion of the A-V timer. The flip-flop 52 is reset upon the occurrence of the next P-wave, or the next atrial pacing pulse which passes through the amplifier 44 by applying a signal on the line 64 to the R, or reset, terminal of the flip-flop 52.

What is claimed is:

1. An implantable cardiac pacer operable in a DVI or DDD mode of pacing comprising:
- means for sensing an atrial pacing pulse or a P-wave pulse sensed from a patient;
- means for providing a predetermined atrial-ventricular timing interval;
- means for sensing the occurrence of an R-wave pulse from the patient;
- means for pacing the ventricular chamber of the patient in the absence of a sensed R-wave during the atrial-ventricular time interval;
- means for providing a predetermined ventricular-atrial timing interval immediately upon the termination of the atrial-ventricular timing interval;
- means for issuing an atrial pacing pulse at the end of the ventricular-atrial timing interval;
- means for determining if an R-wave was sensed during the atrial-ventricular timing interval; and
- means for inhibiting the generation of the ventricular pacing pulse until the end of the atrial-ventricular timing interval in the event that said R-wave was sensed during the atrial-ventricular interval, and for allowing said means for providing a predetermined atrial-ventricular timing interval to provide the entire atrial-ventricular timing interval regardless of whether or not an R-wave was sensed during said atrial-ventricular timing interval.

2. An implantable cardiac pacer operable in a DVI or DDD mode of pacing as claimed in claim 2 wherein said means for determining if an R-wave was sensed during the atrial-ventricular timing interval is a flag-setting means which sets a flag in the event that an R-wave was sensed during said atrial-ventricular timing interval, and said means for inhibiting the generation of the ventricular pacing pulse is responsive to said means for setting said flag.

* * * * *